(12) United States Patent
Shields et al.

(10) Patent No.: US 9,687,240 B2
(45) Date of Patent: Jun. 27, 2017

(54) IMPLANT FOR FACILITATING SUTURELESS SIDE-TO-SIDE ARTERIOVENOUS FISTULA CREATION AND MAINTAINING PATENCY

(71) Applicant: Cook Medical Technologies LLC, Bloomington, IN (US)

(72) Inventors: Adam Shields, Lafayette, IN (US); Keith Milner, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 319 days.

(21) Appl. No.: 14/659,117

(22) Filed: Mar. 16, 2015

(65) Prior Publication Data

US 2015/0257760 A1    Sep. 17, 2015

Related U.S. Application Data

(60) Provisional application No. 61/952,988, filed on Mar. 14, 2014.

(51) Int. Cl.
*A61B 17/11*   (2006.01)
*A61M 1/36*    (2006.01)

(52) U.S. Cl.
CPC .......... *A61B 17/11* (2013.01); *A61M 1/3655* (2013.01); *A61B 2017/1107* (2013.01); *A61B 2017/1139* (2013.01)

(58) Field of Classification Search
CPC .......... A61B 17/11; A61B 2017/1107; A61B 2017/1139; A61B 2017/1103; A61B 17/1114; A61B 17/1128; A61M 1/3655
See application file for complete search history.

(56) References Cited

U.S. PATENT DOCUMENTS

| | | |
|---|---|---|
| 3,254,650 A | 6/1966 | Collito |
| 3,774,615 A | 11/1973 | Lim et al. |
| 4,233,981 A | 11/1980 | Schomacher |
| 4,523,592 A | 6/1985 | Daniel |
| 5,868,763 A | 2/1999 | Spence et al. |
| 6,036,705 A | 3/2000 | Nash et al. |
| 6,179,849 B1 | 1/2001 | Yencho et al. |
| 6,537,287 B1 | 3/2003 | Yencho et al. |
| 6,599,303 B1 | 7/2003 | Peterson et al. |
| 6,616,675 B1 * | 9/2003 | Evard ................ A61B 1/3137 606/153 |
| 6,890,338 B1 | 5/2005 | Davis et al. |
| 6,966,920 B2 | 11/2005 | Yencho et al. |
| 7,351,247 B2 | 4/2008 | Kupiecki et al. |
| 7,497,865 B2 | 3/2009 | Willis et al. |
| 7,591,827 B2 | 9/2009 | Hill et al. |

(Continued)

*Primary Examiner* — Katherine Rodjom
(74) *Attorney, Agent, or Firm* — Brinks Gilson & Lione

(57) ABSTRACT

An anastomosis device for facilitating sutureless side-to-side arteriovenous fistula creation and maintenance of patency thereof is presented. The device comprises two device halves each containing an anastomosis window which is in fluid connection with an interior lumen of the device. Further, the device comprises a pair of vessel joining portions in which the bounds of the fistula are created. The invention also has an embodiment wherein a method of joining a vein and an artery in order to create a fistula is presented.

17 Claims, 3 Drawing Sheets

(56) References Cited

U.S. PATENT DOCUMENTS

| | | | |
|---|---|---|---|
| 7,892,246 B2* | 2/2011 | Akin | A61B 17/11 606/153 |
| 7,892,247 B2 | 2/2011 | Conston et al. | |
| 8,109,949 B2 | 2/2012 | Blatter et al. | |
| 8,361,092 B1 | 1/2013 | Asfora | |
| 2004/0204724 A1 | 10/2004 | Kissel et al. | |
| 2005/0043752 A1* | 2/2005 | Phan | A61B 17/064 606/155 |
| 2006/0282106 A1 | 12/2006 | Cole et al. | |
| 2008/0119879 A1 | 5/2008 | Brenneman et al. | |

* cited by examiner

IMPLANT FOR FACILITATING SUTURELESS SIDE-TO-SIDE ARTERIOVENOUS FISTULA CREATION AND MAINTAINING PATENCY

CROSS REFERENCE TO RELATED APPLICATIONS

This application claims the benefit of U.S. Provisional Patent Application No. 61/952,988, filed on Mar. 14, 2014, the entire contents of which is hereby incorporated by reference.

BACKGROUND OF THE INVENTION

Field of Invention

The present invention relates to medical devices. More particularly, the invention relates to an implant which in one embodiment facilitates sutureless side-to-side arteriovenous fistula (AVF) creation and maintains the patency thereof.

Background

End-stage renal disease (ESRD) is a growing problem in the United States and abroad, with the number of patients requiring treatment far outstripping the number of donor kidneys available. Those patients who are unable to receive a kidney transplant are treated by dialysis, with roughly ten times as many patients receiving hemodialysis as all other forms combined.

To minimize treatment time, hemodialysis requires a large blood volume flow rate. Increasing flow is typically achieved through the surgical creation of an arteriovenous shunt. This creates a low resistance pathway, significantly increasing flow through a graft or an arteriovenous fistula.

In practice, AVF is preferred to graft usage because fistulas have better long-term patency rates and reduced incidences of secondary interventions after creation. However, the surgical creation of an AVF and the subsequent venous tissue remodelling required to realize optimized flow rates is only successful in approximately half of surgical procedures. Failures involving AVF are largely due to stenosis via neointimal hyperplasia and thrombosis. A potential cause of neointimal hyperplasia is the exposure of venous tissue to the abnormal hemodynamic conditions resulting from significantly increased flow rates and pulsatility of the added arterial blood flow. In other cases, large flow rates can cause extreme dilation and result in oversized fistulas which fail to achieve the purpose for which they were created.

There exists a need for an improved method of creating arteriovenous fistula and maintaining the patency thereof, including implantation of devices designed to achieve these purposes.

BRIEF SUMMARY OF THE INVENTION

The present invention provides a first device half having a first proximal end and a first distal end, the first device half comprising a first inner surface and a first outer surface opposite the first inner surface, the first device half having a first anastomosis window formed therethrough defining a first arch and a second arch opposite the first arch; a second device half having a second proximal end and a second distal end, the second device half comprising a second inner surface and a second outer surface opposite the second inner surface, the second device half having a second anastomosis window formed therethrough defining a third arch and a fourth arch opposite the third arch; a connecting tube having a first end and a second end opposite the first end, the connecting tube having a lumen formed through the first end and second along a longitudinal axis of the connecting tube, the first end being connected to the first inner surface of the first device half at the first anastomosis window, the second end being connected to the second inner surface of the second device half at the second anastomosis window so that the first anastomosis window is in fluid connection with the second anastomosis window; the connecting tube comprising a circumferential surface having a first area and a second area, the first area being between the first arch and the third arch and having a plurality of first barbs disposed thereon and arranged in a first pair of rows spaced apart oppositely from each other and substantially normal to the longitudinal axis, the first barbs extending inwardly; and the second area being between the second arch and the fourth arch and having a plurality of second barbs disposed thereon and arranged in a second pair of rows spaced apart oppositely from each other and substantially normal to the longitudinal axis, the second barbs extending inwardly.

In another embodiment the present invention provides a step of incising the vein wall substantially longitudinally to provide a first vein lip and a second vein lip, defining a vein aperture; a step of incising the vein wall substantially longitudinally to provide a first artery lip and a second artery lip, defining an artery aperture; and a step of implanting an anastomosis device to form the side-to-side fistula, the anastomosis device comprising: a first device half having a first proximal end and a first distal end, the first device half comprising a first inner surface and a first outer surface opposite the first inner surface, the first device half having a first anastomosis window formed therethrough; a second device half having a second proximal end and a second distal end, the second device half comprising a second inner surface and a second outer surface opposite the second inner surface, the second device half having a second anastomosis window formed therethrough; a connecting tube having a first end and a second end opposite the first end, the connecting tube having a lumen formed through the first end and second along a longitudinal axis of the connecting tube, the first end being connected to the first inner surface of the first device half at the first anastomosis window, the second end being connected to the second inner surface of the second device half at the second anastomosis window so that the first anastomosis window is in fluid connection with the second anastomosis window; the connecting tube comprising a circumferential surface having a first area and a second area, the first area having a plurality of first barbs disposed thereon and arranged in a first pair of rows spaced apart oppositely from each other and substantially normal to the longitudinal axis, the first barbs extending inwardly; and the second area having a plurality of second barbs disposed thereon and arranged in a second pair of rows spaced apart oppositely from each other and substantially normal to the longitudinal axis, the second barbs extending inwardly to facilitate side-to-side fistula.

Further objects, features, and advantages of the present invention will become apparent from consideration of the following description and the appended claims when taken in connection with the accompanying drawings.

DETAILED DESCRIPTION OF THE INVENTION

Figure 1A:
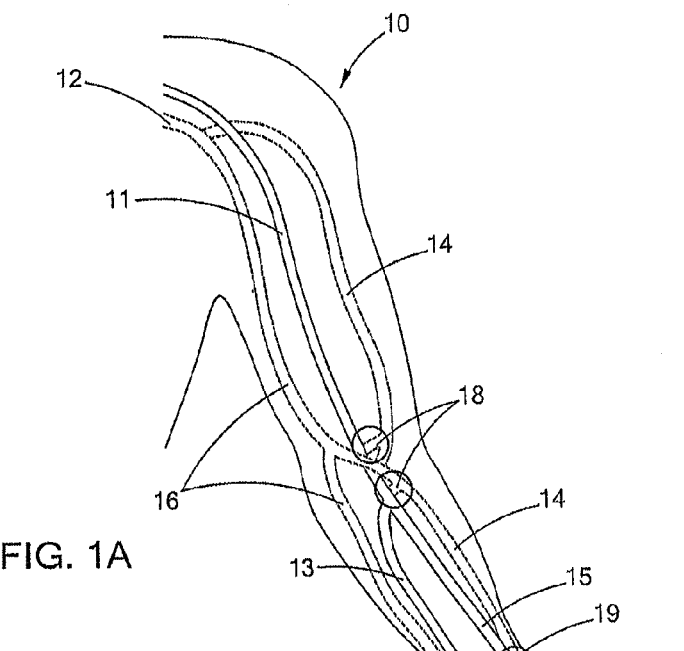
FIG. 1A is diagram of major arteries and veins of the human arm and selected arteriovenous fistulas that may be created therein.

The following provides a detailed description of currently preferred embodiments of the present invention. The description is not intended to limit the invention in any manner, but rather serves to enable those skilled in the art to make and use the invention.

In this description, when referring to a device, the term distal is used to refer to an end of a component which in use is furthest from the physician during the medical procedure, including within a patient. The term proximal is used to refer to an end of a component closest to the physician and in practice in or adjacent an external manipulation part of the deployment or treatment apparatus. Similarly, when referring to an implant such as an anastomosis device the term distal is used to refer to an end of the device which in use is furthest from the physician during the medical procedure and the term proximal is used to refer to an end of the device which is closest to the physician during the medical procedure.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part.

The present disclosure generally provides an implant or device which facilitates the formation of an arteriovenous fistula and maintaining the patency thereof. Surgical fistula creation is presently the preferred method of increasing blood flow for ESRD patients who are receiving hemodialysis. The advantages of fistulas over such treatments as grafts are numerous. For instance, of the treatment methods for ESRD patients that might be used to increase blood flow rates, AVFs are associated with decreased morbidity and mortality, and have the superior primary patency rates, the lowest rates of thrombosis, and require the fewest secondary interventions. AVFs generally provide longer hemodialysis access survival rates. Medical data shows that the total number of interventions during the life of the access is considerably lower for AVFs compared with AV grafts and that AVFs have lower rates of infection than AV grafts. The danger of infection is also decreased upon successful formation of an AVF. Thus, it is not surprising that AVFs also lead to lower hospitalization rates among ESRD patients who undergo some form of treatment to increase blood flow rates in order to facilitate hemodialysis.

However, there is a need to improve the ways that AVFs are created and maintained. Fewer than 15% of dialysis fistulas remain patent and can function without problems during the entire period of a patient's dependence on hemodialysis. The mean problem-free patency period after creation of native fistulas is approximately 3 years, whereas prosthetic polytetrafluoroethylene (PTFE) grafts last 1-2 years before indications of failure or thrombosis are noted. After multiple interventions to treat underlying stenosis and thrombosis, the long-term secondary patency rates for native fistulas are reportedly 7 years for fistulas in the forearm and 3-5 years for fistulas in the upper arm. Prosthetic grafts remain patent for up to 2 years.

For prosthetic grafts, fistula failure and eventual occlusion occur most commonly as a result of the progressive narrowing of the venous anastomosis; for native fistulas, failure occurs most commonly as a result of the narrowing of the outflow vein. The primary underlying pathophysiologic mechanism responsible for causing the failure is intimal hyperplasia at the anastomotic site. Additional causes include surgical and iatrogenic trauma, such as repeated venipunctures. Stenoses along the venous outflow and in intragraft locations (for prosthetic PTFE grafts) are also common.

The embodiments of the device described herein are designed in part to overcome these deficiencies. The anastomosis device provides a luminal region with a defined geometry for blood flow therethrough. It also provides a limited amount of contact between the intimal surfaces of the vessels to be connected by the fistula relative to methods of directly connecting the artery and the vein surgically.

Another aspect of the present device is ability to create a fistula in a sutureless fashion. Suturing of delicate vessels is technically challenging and extends the time of procedures. By configuring the fistula and the device in such a way as to avoid a suturing step, the intervention is made simpler and faster.

Referring to FIG. 1A, the veins and arteries of the arm are illustrated. Fistulas in ESRD patients are generally created in the arm. Arm 10 contains a plurality of arteries (illustrated in solid lines) and veins (illustrated in dashed lines.) Brachial artery 11 originates toward the shoulder and splits into an ulnar artery 13 and a radial artery 15 in the region of the elbow. Likewise, axillary vein 12 and cephalic vein 14 run through the shoulder region, and in the area of the elbow, the axillary vein 12 splits into the basilic vein 16. The vessels that were previously split, arteries and veins alike, can undergo anastomosis and form fistulas. Exemplary fistulas illustrated include brachial-cephalic arteriovenous fistula 18, between the brachial artery 11 and the cephalic vein 14, and radial-cephalic fistula 19, between the radial artery and the cephalic vein 14.

Figure 1B:
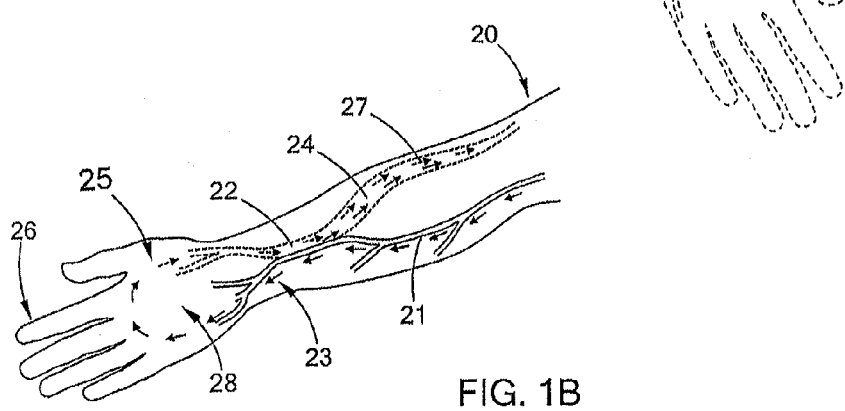
FIG. 1B is a diagram of blood flow through an arteriovenous fistula surgically created in a human forearm.

FIG. 1B illustrates an example of the blood flow consequences of arteriovenous fistula creation. Artery 21 carries arterial blood 23 away from the heart and through the arm 20 in the direction of hand 26. Arteriovenous fistula 29 connects the artery 21 to vein 22. A portion of the blood flows through fistula 29 and the remainder continues on its natural path through the capillary system 28 in the hand. In the capillaries the blood deoxygenates and flows as venous flow 25 through the vein 22. Due to the fistula, a combined arterial-venous blood flow 27 forms, and as a result of the increased volume and flow rate of blood through the vasculature, an enlarged portion 24 of the vein arises.

Figure 2A:
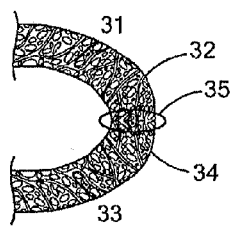
FIGS. 2A-2C are schematic representations of end-to-end, side-to-end, and side-to-side arteriovenous fistulas, respectively.
Figure 2B:
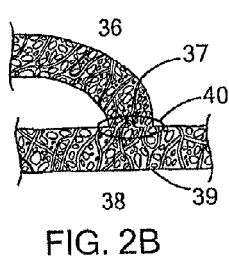
Figure 2C:
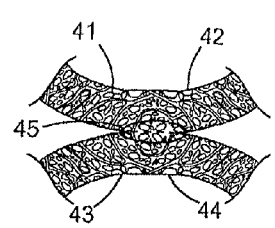

FIGS. 2A-C are examples of different configurations of arteriovenous fistula. FIG. 2A illustrates an artery 31 with an artery end 32 as well as a vein 33 having a vein end 34. The artery end 32 is joined to vein end 34 to form end-to-end arteriovenous fistula 35. Such a fistula configuration can be technically difficult to execute and has an intrinsic disadvantage as artificial creation of an end-to-end fistula naturally requires that the vessels used in its formation be completely severed in order to connect the ends, thereby completely disconnecting the vessels from the rest of the vascular system.

FIG. 2B instead shows artery 38 with artery end 39 and vein 36 with vein wall 37. The artery end 39 is attached to vein 36 through vein wall 38 to form side-to-end arteriovenous fistula 40. This type of fistula is technically simpler to execute for a surgeon but still has the drawback that the vessel whose end it used (in the case illustrated, artery 38 with artery end 39) has its downstream regions disconnected from the rest of the vascular system. This complete rerouting of the blood flow can have negative consequences.

An alternative fistula arrangement, the side-to-side arteriovenous fistula, is illustrated in FIG. 2C. In this example, artery 41 has been perforated through artery wall 42 and joined to vein 43 through vein wall 44 to create side-to-side fistula 45. Because of the side-to-side configuration, a portion of the blood continues to flow in the natural pattern to downstream tissues, unlike the case in which an artery end or a vein end is employed to create the anastomosis. However, even creation of this type of AVF can be difficult using standard surgical techniques. A properly-designed device can simplify the procedure and, importantly, maintain patency of the AVF.

Figure 3A:
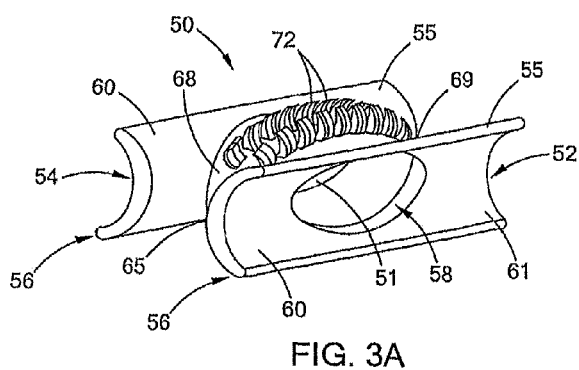
FIG. 3A is a perspective view of one embodiment of an anastomosis device.

FIG. 3A illustrates a device 50 in accordance with one embodiment of the present invention. Device 50 has a proximal end 52 and a distal end 54. It should be noted, however, that because of the symmetry between the proximal ends and distal ends, that these designations are arbitrary and employed for purposes of convenience. The device is made of two device halves 60 comprising a first device half and a second device half. In the embodiment illustrated in FIG. 3, the device halves 60 extend between proximal end 52 and distal end 54.

Figure 3B:
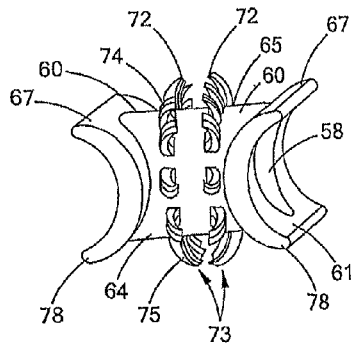
FIG. 3B is a side view of the anastomosis device of FIG. 3A.

As shown in FIG. 3B, between the device halves 60 is connecting tube 64. This tube surrounds lumen 51, has a longitudinal axis running through it, and is in fluid connection with anastomosis windows 58 which are formed through the outer device walls 61. The lumen 51 through connecting tube 64 can serve to function as the conduit through which blood flows, functionally providing the AVF.

In one embodiment, the connecting tube 64 is substantially cylindrical in shape and has a circumference. In such an embodiment, cross-sections taken normal to the longitudinal axis will result in circles. In another embodiment, the connecting tube 64 may be substantially prismatic or may have substantially square or rectangular cross sections normal to the longitudinal axis.

The device halves 60 have a first portion 67 and a second portion 78. The device halves 60 also have an inner surface which provides a boundary for the lumen 51 and also have a portion that does not face the lumen 51. This latter portion is referred to as outer device wall 61. Outer device wall 61 is encompassed by portions of first arch 62 and second arch 63 and all other portions of device half 60 that are opposite to the lumen 51. Outer device wall 61 curves away from the lumen 51, giving each device a "C" shape when viewed head-on and giving the device 50 a butterfly shape when viewed in profile. However, the overall shape of the device and the shape of each device half can take on numerous forms. In the illustrated embodiment, the device halves are substantially concave, but the device halves can also be substantially flat or substantially convex as long as it is possible to maintain sutureless anastomosis and as long as the ability to connect the vessel walls at the portions of the device such as a vessel-connecting space described below is retained. In some embodiments, the device may be substantially as depicted in FIG. 3A, but also comprising a projection or ridge extending from the upper arch or the lower arch, or both, off of the outer surface of the device. In such an instance, the device would appear to have a connecting tube which extends beyond the plane of each anastomosis window.

In an embodiment where there is a first device half and a second device half, the first device half comprises a first arch and a second arch opposite the first arch. The second device half of this embodiment comprises a third arch and a fourth arch opposite the third arch.

The embodiment of device 50 shown in FIG. 3A-3B further comprises a pair of flanges at each end. Each device half 60 has a proximal flange 55 at proximal end 52 and a distal flange 56 at distal end 54. The proximal flange 55 and the distal flange 56 extend in the proximal and distal directions, respectively, beyond proximal-most portion 69 and distal-most portion 68, which represent the outer bounds of the outer surface of connecting tube 64. The proximal flange 55 of one device half 60 is not in contact with the proximal flange 55 of the other device half 60, being separated by inner flange gap 65. The distal flanges 56 are constructed in a similar manner, also being separated and having an inner flange gap 65 separating the two distal flanges 57.

The device 50 in accordance with the principles of the present invention has a plurality of first barbs 72 which assist in the gripping and stabilization of portions of vessel walls which are to be secured to the device. The first barbs 72 and the second barbs 73 are formed along the circumferential surface of the connecting tube 64. The points are capable of securing the vascular material but are not sharp enough to pierce and damage it. In the embodiment depicted, the barbs are arranged in two rows with a space between them in spaced-apart fashion and with the each of the plurality of barbs pointing inwardly toward each other, although other configurations are possible. In such a configuration, each of the pluralities of first barbs 72 are spaced apart to create a first space for receiving a portion of at least one vessel therebetween, and each of the pluralities of second barbs 73 are spaced apart similarly to create a first space for receiving a portion of at least one vessel therebetween.

In an embodiment where there is a first device half and a second device half, the first device half comprises a first arch and a second arch opposite the first arch. The second device half of this embodiment comprises a third arch and a fourth arch opposite the third arch. In such an arrangement, the outer surface of the connecting tube can be divided into a first area that is positioned between the first arch and the third arch, and a second area that is positioned between the second arch and the fourth arch. In this way a pair of rows of barbs in alignment with one another can be placed in the first area to create a space between the barb rows which is substantially normal a longitudinal-most dimension of the outer surface of the tube. Likewise, a pair of rows of barbs in alignment with one another can be placed in the second area to create a space between the barb rows which is substantially normal a longitudinal-most dimension of the outer surface of the tube. Thus, in this embodiment it will be possible to draw a line which passes through the first arch, a barb from a first row of barbs, a barb from the row of barbs facing that first row of barbs, and then the third arch.

It is to be noted that "circumferential surface" is not limited to cylindrical embodiments but when the cross-section of a device is not circular the "circumferential surface" should be interpreted instead as a perimeter surface extending around the body of the connecting tube and comprising a plane.

In an embodiment wherein the connecting tube 64 is substantially cylindrical, the plurality of first barbs 72 may be arranged substantially circumferentially opposite the plurality of second barbs 73, or a 180 degree spacing around the circumference of the connecting tube 64. In such an embodiment, each plurality of first barbs 72 and second barbs 73 would lie on a circumferential segment of a circular cross-section of the cylindrical connecting tube 64, and would lie on a plane which lies normal the longitudinal axis which runs through the center of the cylindrical connecting tube 64. In one embodiment the pluralities of first barbs and second barbs positioned closest the same device half may effectively run into one another, with barbs spaced around the entire circumference of a circular cross section of the connecting tube 64.

In an embodiment wherein the connecting tube 64 is substantially prismatic, such as when it has a rectangular or square cross-section, the plurality of first barbs 72 may be arranged on a first face of the prismatic connecting tube 64 and the plurality of second barbs 73 may be arranged on a second face of the prismatic connecting tube 64, the first face being opposite the second face.

A barb can have two ends, including the end which comprises a portion of the device from which it extends, and the barb can then extend to a second end, which may be a point. Each point is capable of securing the vascular material but are not sharp enough to pierce and damage it. The barbs may curve and have a dentite or bladelike shape. A barb that is considered to be pointing inward extends in a roughly opposite direction from the outer surface of the device half from which it originates and toward the opposite device half. Such a barb may be integrally formed with the device halves, such as by an additive manufacturing process, including 3D printing, and formed unitarily with the remainder of the device. Barbs may also extend outward, in which case the barbs extend to their points which are oriented toward the outer surface of the device half closest to that upon which they are formed.

As mentioned previously, when there are no features of the device which impart a directionality or introduce an asymmetrical element to it, and the device is outside a surgical context (that is, it is not being used at that moment in a procedure or has not been implanted into a patient), the terms proximal and distal can be switched with one another. The terms first and second can be switched in a similar fashion. However, the outer portion of the device, including outer device walls 61, will remain an outer or exterior portion, and the lumen 51 will remain interior, regardless of the designation of first/second and proximal/distal.

An anastomosis device 50 with the structural features described herein can be made of a number of different materials. Such a device 50 can be made of a biocompatible and biologically-inert material which will be well-tolerated by the tissues it contacts but will not encourage, for instance, growth of new intimal tissue across its openings. The device 50 can be made of a variety of polymers, including photosensitive polymers which are used for rapid prototyping applications. The polymers can have a stiffness ranging from relatively labile to relatively stiff, taking into account that the integrity of the anastomosis windows 58 must be maintained for optimal operation of the device. The device 50 may also be coated or impregnated with drugs which will prevent or slow endothelialization of the anastomosis windows 58 and thereby reduce the space available for blood flow through the AVF. The device may be made by a number of processes, including injection molding.

The slits to be cut into the artery walls and vein walls to provide openings for blood flow, when used in a device in accordance with an embodiment of the present invention will be made parallel to the direction of blood flow or substantially longitudinally. Put another way, the slitting is done parallel to a longitudinal axis of the vessel to be slit. However, slitting in any direction may be amenable so long as anastomosis can still be facilitated. In many cases be about one centimeter in length. Therefore, a device 50 will have an anastomosis window 58 which extends for slightly greater than one centimeter in the proximal-to-distal dimension. It is possible that a favorable increase in blood flow through an AVF can be achieved with a fistula which is less than one centimeter wide, in which case it will be acceptable to construct a device 50 with an anastomosis window 58 which is less than 1 centimeter wide as well. Contrarily, certain patients may require that an AVF longer than one centimeter wide be constructed. In such cases, a device which has a longer anastomosis window 58 than one centimeter will be best suited for facilitating hemodialysis in such patients. The overall diameter of the device, as measured from one anastomosis window to another, may be about five to ten millimeters across.

Figure 4A:
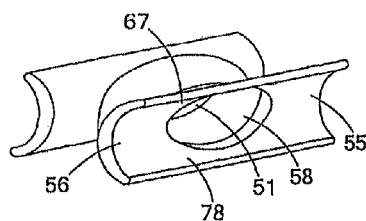
FIGS. 4A-4B are simplified perspective views of the device halves of anastomosis devices in accordance with further embodiments of the invention.
Figure 4B:
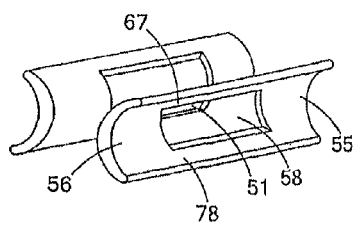

FIGS. 4A-4B are simplified perspective views of devices 50 in accordance with embodiments of the present invention. These views illustrate how the anastomosis window 58 comprises the open portions of the connecting tube 65 through the outer device walls 61. The anastomosis window 58 can take on a variety of shapes. In the preferred embodiment of FIG. 4A, the anastomosis window 58 has a substantially elliptical shape. The dimensions of the ellipse confer certain advantages on the device. For instance, the larger axis of the ellipse provides a way of incorporating the entire length of the AVF which is formed from slitting the vessels within the anastomosis window 58, while the smaller axis of the ellipse further defines the geometry of the anastomosis and ensures that the dimensions of the device do not greatly exceed the height of the vessels involved. Likewise, a device according to the embodiment of FIG. 4B, in which the anastomosis window 58 is a rectangle having a greater length than height dimension, would confer similar advantages to the elliptical window of FIG. 4A. These embodiments, however, are not intended to be limiting. Devices having anastomosis windows 58 in various shapes, including squares, circles, or other polygonal shapes are also envisioned as acceptable alternative embodiments to those illustrated.

Figure 5A:
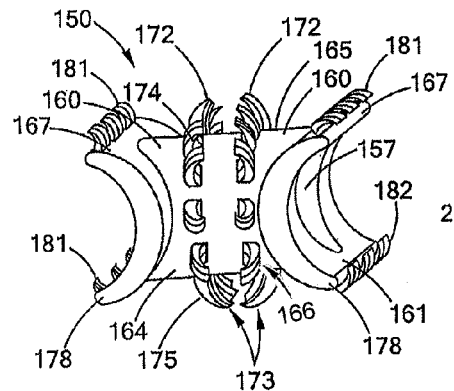
FIGS. 5A-5B are perspective views of two more embodiments of an anastomosis device in accordance with the present invention.

FIG. 5A shows an alternative embodiment of a device 150 in accordance with the principles of the present device. In this embodiment, device 150 comprises device halves 160 which are connected by connecting tube 164, which is in fluid connection with anastomosis windows 157, which are formed substantially centrally through outer surfaces 161. A pair of first barbs 172 are positioned on a first (or upper) half 165 of the circumferential surface of connecting tube 164 and are disposed pointing inwardly, facing one another, creating a first vessel-connecting space 174 between the rows off inward-facing, opposing first barbs. A pair of second barbs 173 are disposed on a second (or lower) half 166 of the circumferential surface of connecting tube 164 and are disposed pointing inwardly, facing one another, creating a second vessel-connecting space 175 between the rows of inward-facing, opposing second barbs. An additional feature of a device in this embodiment are a plurality of second first barbs 181 located at the first portion 167 of the device 150 and a plurality of second barbs 182 located along the second portion 178. These second first barbs 181 and second second barbs 182 can provide an extra means of gripping the vessels from the inside during and after the implantation procedure.

Figure 5B:
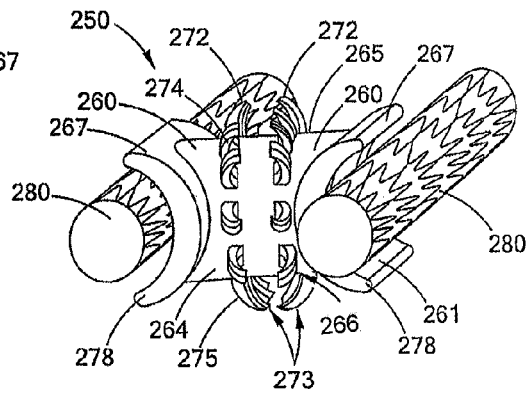

FIG. 5B depicts yet another alternative embodiment of a device in accordance with the principles of the present invention. In this embodiment, device 250 comprises device halves 260 having a first (or upper) portion 267 opposite second (or lower) portion 278. The device halves 260 are connected by connecting tube 264, which is in fluid connection with anastomosis windows 257, which are formed substantially centrally through outer surfaces 261. A pair of first barbs 272 are positioned on a first (or upper) half 265 of the circumferential surface of connecting tube 264 and are disposed pointing inwardly, facing one another, creating a first vessel-connecting space 274 between the rows off inward-facing, opposing first barbs. A pair of second barbs 273 are disposed on a second (or lower) half 266 of the circumferential surface of connecting tube 264 and are disposed pointing inwardly, facing one another, creating a second vessel-connecting space 275 between the rows of inward-facing, opposing second barbs. In this embodiment, device 250 has a similar structure to the devices of the previous embodiments, except that a pair of expandable stents 280 have been attached to outer device walls 261. The expandable stents 280 obscure the view of anastomosis windows 257 in FIG. 5B, but the struts of the stent structure are spaced such that the interior portions of the stents 280 are in fluid connection with the anastomosis windows 257 and therefore tube lumen 251. As the device is implanted within a patient, the stents 280 are placed within the interior or lumen of the affected artery and vein. The stents 280 are preferably made of a shape memory material. In one embodiment the shape memory material is a nickel-titanium alloy. In one embodiment, the stents 280 are ZILVER® stents. When the device 250 is implanted, the stents reach body temperature and expand within the vasculature to their remembered state, stabilizing the device and the AVF at the same time.

Referring now to FIGS. 6A-6D, a method of creating an arteriovenous fistula in accordance with one embodiment of this invention is illustrated. A person having skill in the art will appreciate that variations to the process are possible beyond what is illustrated in FIGS. 6A-6D without deviating from the spirit of the present invention.

Figure 6A:
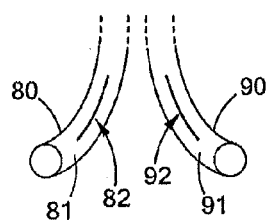
FIGS. 6A-D are schematic views of the steps of one embodiment of a method of creating and stabilizing a fistula in accordance with another aspect of the present invention.

FIG. 6A illustrates a vein 80 and an artery 90 which are to be used in the creation of an AVF. The vein 80 is bounded by vein wall 81 and the artery 90 by artery wall 91. A vein slit 82 has been formed through vein wall 81 to form an aperture and an artery slit 92 has been formed to give rise to an aperture through artery wall 91. The slits may be made by any acceptable means, including by scalpel.

Figure 6B:
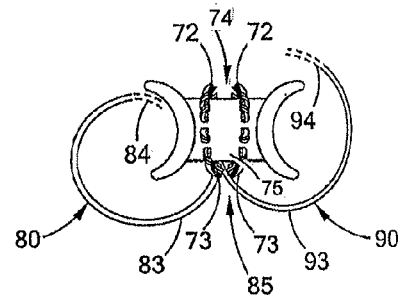

Referring now to FIG. 6B, the vessels have been opened. The vein 80 has been opened along vein slit 82 to divide the vein 80 into second vein lip 83 and first vein lip 84. Likewise, the artery 90 has been opened along artery slit 92 to create first artery lip 94 and second artery lip 93. The second vein lip 83 and the second artery lip 93 have been inserted between the rows of opposing second barbs 73. The position at which the vessels meet is first arteriovenous junction 85.

Figure 6C:
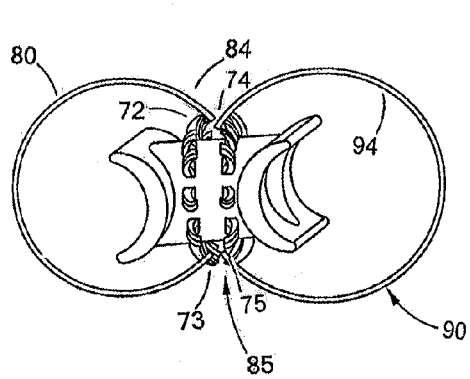

FIG. 6C illustrates a third step in the sutureless AVF creation procedure. In this step the first vein lip 84 and the first artery lip 94 have been inserted between the rows of opposed first barbs 72. The first vein lip 84 and the first artery lip 94 are secured thereon. At this point the majority of the device is contained within the interior of the vein 80 and of the artery 90, and any second first or second barbs or expandable stents attached to the device have functioned to secure the vessels.

Figure 6D:
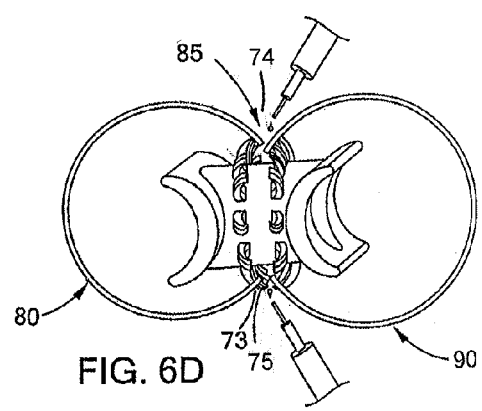

FIG. 6D illustrates the final step in placement of the device 50. The first vein lip 84 and the first artery lip 94 meet at second arteriovenous junction 95. The first arteriovenous junction 85 and the second arteriovenous junction 95 are sealed in a sutureless manner. One way of achieving this is by sealing with a surgical glue such as fibrin glue. Now the AVF has been created and blood is flowing through the anastomosis window from the artery 90 into the lumen 51 created by the connecting tube and then into the vein 80.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. A device for facilitating side-to-side arteriovenous fistula comprising:
    a first device half having a first proximal end and a first distal end, the first device half comprising a first inner surface and a first outer surface opposite the first inner surface, the first device half having a first anastomosis window formed therethrough defining a first arch and a second arch opposite the first arch;
    a second device half having a second proximal end and a second distal end, the second device half comprising a second inner surface and a second outer surface opposite the second inner surface, the second device half having a second anastomosis window formed therethrough defining a third arch and a fourth arch opposite the third arch; and
    a connecting tube having a first end and a second end opposite the first end, the connecting tube having a lumen formed through the first end and second along a longitudinal axis of the connecting tube, the first end being connected to the first inner surface of the first device half at the first anastomosis window, the second end being connected to the second inner surface of the second device half at the second anastomosis window so that the first anastomosis window is in fluid connection with the second anastomosis window, the connecting tube comprising a circumferential surface having a first area and a second area opposite the first area, the first area being between the first and the third arches, the second area being between the second and the fourth arches, the first area having a plurality of first barbs disposed thereon and arranged in a first pair of rows spaced apart oppositely from each other and substantially normal to the longitudinal axis, the first barbs extending inwardly, and the second area having a plurality of second barbs disposed thereon and arranged in a second pair of rows spaced apart oppositely from each other and substantially normal to the longitudinal axis, the second barbs extending inwardly.

2. The device of claim 1 wherein the proximal ends of the device halves further comprise a pair of proximal flanges extending beyond a proximal portion of the connecting tube, and wherein the distal ends of the device halves define a pair of distal flanges extending beyond a distal portion of the connecting tube.

3. The device of claim 2 wherein the proximal flanges are not in contact, defining a proximal flange gap between them, and wherein the distal flanges are not in contact, defining a distal flange gap between them.

4. The device of claim 1 having anastomosis windows that are substantially elliptical.

5. The device of claim 1 having anastomosis windows that are substantially rectangular.

6. The device of claim 1 wherein the connecting tube is substantially cylindrical.

7. The device of claim 1 wherein the connecting tube is substantially prismatic.

8. The device of claim 7 wherein the connecting tube has a cross section which is substantially square in shape.

9. The device of claim 7 wherein the connecting tube has a cross section which is substantially rectangular in shape.

10. The device of claim 1 further comprising a plurality of outer barbs extending from an outer surface of the device halves, the plurality of outer barbs being configured to point away from the device body.

11. A method of facilitating side-to-side fistula along a longitudinal portion of a vein and an artery, the vein having a vein wall, the artery having an artery wall, the method comprising:
    incising the vein wall substantially longitudinally to provide a first vein lip and a second vein lip, defining a vein aperture;
    incising the vein wall substantially longitudinally to provide a first artery lip and a second artery lip, defining an artery aperture;
    implanting an anastomosis device to form the side-to-side fistula, the anastomosis device comprising: a first device half having a first proximal end and a first distal end, the first device half comprising a first inner surface and a first outer surface opposite the first inner surface, the first device half having a first anastomosis window formed therethrough; a second device half having a second proximal end and a second distal end, the second device half comprising a second inner surface and a second outer surface opposite the second inner surface, the second device half having a second anastomosis window formed therethrough; a connecting tube having a first end and a second end opposite the first end, the connecting tube having a lumen formed through the first end and second along a longitudinal axis of the connecting tube, the first end being connected to the first inner surface of the first device half at the first anastomosis window, the second end being connected to the second inner surface of the second device half at the second anastomosis window so that the first anastomosis window is in fluid connection with the second anastomosis window; the connecting tube comprising a circumferential surface having a first area and a second area, the first area having a plurality of first barbs disposed thereon and arranged in a first pair of rows spaced apart oppositely from each other and substantially normal to the longitudinal axis, the first barbs extending inwardly; and the second area having a plurality of second barbs disposed thereon and arranged in a second pair of rows spaced apart oppositely from each other and substantially normal to the longitudinal axis, the second barbs extending inwardly to facilitate side-to-side fistula.

12. The method of claim 11 wherein implanting comprises:
    disposing the second artery lip and the second vein lip between the pair of rows of second barbs such that the second arch is disposed inside the wall of the vein and the fourth arch is disposed inside the wall of the artery;
    joining the second artery lip to the second vein lip;
    disposing the first artery lip and the first vein lip between the pair of rows of first barbs such that the first arch is disposed inside the wall of the vein and the third arch is disposed inside the wall of the artery; and
    joining the first artery lip to the first vein lip.

13. The method of claim 12 further comprising a step of securing the first vein lip on at least one of the plurality of first barbs.

14. The method of claim 12 further comprising a step of securing the first artery lip on at least one of the plurality of first barbs.

15. The method of claim 12 further comprising a step of securing the second vein lip on at least one of the plurality of second barbs.

16. The method of claim 12 further comprising a step of securing the second artery lip on at least one of the plurality of second barbs.

17. The method of claim 12 wherein joining an artery lip to a vein lip comprises connecting with surgical glue.

* * * * *